(12) United States Patent
Rubin

(10) Patent No.: US 8,316,581 B2
(45) Date of Patent: *Nov. 27, 2012

(54) COMPRESSED GROWING MEDIUM

(76) Inventor: Patti D. Rubin, Aventura, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/348,239

(22) Filed: Jan. 11, 2012

(65) Prior Publication Data

US 2012/0103038 A1 May 3, 2012

Related U.S. Application Data

(60) Continuation of application No. 12/368,216, filed on Feb. 9, 2009, which is a division of application No. 10/993,599, filed on Nov. 19, 2004, now abandoned.

(51) Int. Cl.
  *A01G 31/00* (2006.01)
(52) U.S. Cl. .................................. 47/58.1 SC
(58) Field of Classification Search .............. 47/58.1 SC
  See application file for complete search history.

(56) References Cited

U.S. PATENT DOCUMENTS

| | | |
|---|---|---|
| 507,144 A | 10/1893 | Lundell |
| 1,827,051 A | 10/1931 | Thomas |
| 2,450,830 A | 10/1948 | Helberg |
| 2,508,414 A | 5/1950 | Meyer |
| 2,664,404 A | 12/1953 | Brandon |
| 2,917,379 A | 12/1959 | Ryker |
| 2,971,292 A | 2/1961 | Malecki |
| 2,998,550 A | 8/1961 | Collins et al. |
| 3,284,209 A | 11/1966 | Kelly |
| 3,375,607 A | 4/1968 | Melvold |
| 3,396,810 A | 8/1968 | Andrews |
| 3,502,458 A | 3/1970 | Schenk |
| 3,524,279 A | 8/1970 | Adams |
| 3,590,937 A | 7/1971 | Andrews |
| 3,615,809 A | 10/1971 | Haynes, Jr. et al. |
| 3,653,459 A | 4/1972 | Andrews |
| 3,656,930 A | 4/1972 | Martin |
| 3,656,932 A | 4/1972 | Scheuermann |
| 3,669,204 A | 6/1972 | Andrews |
| 3,703,464 A | 11/1972 | Ferm |
| 3,733,745 A | 5/1973 | Paabo |
| 3,809,175 A | 5/1974 | Andrews |
| 3,842,537 A | 10/1974 | Bishop |
| 3,960,722 A | 6/1976 | Tomikawa |
| 3,962,823 A | 6/1976 | Zipperer |
| 3,973,355 A | 8/1976 | McKenzie |

(Continued)

FOREIGN PATENT DOCUMENTS

CA 1328744 C 4/1994

(Continued)

OTHER PUBLICATIONS

"Coir Could Quickly Gain Share in Growing Media Market" Henry Martinez Greenhouse Management & Production Jul. 1995 (2 pgs.).

(Continued)

*Primary Examiner* — Frank T Palo
(74) *Attorney, Agent, or Firm* — Holland & Hart LLP

(57) ABSTRACT

A growing medium includes a bulking agent and a water-retentive polymer blended together and compressed at a volume-to-volume ratio ranging from about 2:1 to about 10:1, being substantially free of a water-soluble binder material.

20 Claims, 9 Drawing Sheets

U.S. PATENT DOCUMENTS

| | | |
|---|---|---|
| 4,051,628 A | 10/1977 | Knapp et al. |
| 4,072,794 A | 2/1978 | Tomita et al. |
| 4,098,398 A | 7/1978 | Meyers |
| 4,123,418 A | 10/1978 | Gilg et al. |
| 4,128,508 A | 12/1978 | Munden |
| 4,172,039 A | 10/1979 | Akiyama |
| 4,174,957 A | 11/1979 | Schwartz et al. |
| 4,185,987 A | 1/1980 | Tilkanen |
| 4,258,659 A | 3/1981 | Rowell |
| 4,277,345 A | 7/1981 | Heitkamp |
| 4,318,248 A | 3/1982 | Muldner |
| 4,341,180 A | 7/1982 | Cortigene et al. |
| 4,351,754 A | 9/1982 | Dupre et al. |
| 4,407,092 A | 10/1983 | Ware |
| 4,424,645 A | 1/1984 | Rannali |
| 4,473,390 A | 9/1984 | Teufel et al. |
| 4,537,877 A | 8/1985 | Ericsson |
| 4,551,165 A | 11/1985 | Warner |
| 4,570,573 A | 2/1986 | Lohman |
| 4,579,578 A | 4/1986 | Cooke |
| 4,591,635 A | 5/1986 | Greve et al. |
| 4,627,382 A | 12/1986 | Muzzey |
| 4,643,811 A | 2/1987 | Langlois et al. |
| 4,643,814 A | 2/1987 | Goldstein |
| 4,675,388 A | 6/1987 | Greve et al. |
| 4,705,248 A | 11/1987 | McIntyre |
| 4,721,059 A | 1/1988 | Lowe et al. |
| 4,723,510 A | 2/1988 | Skillestad |
| 4,734,393 A | 3/1988 | Lowe et al. |
| 4,738,286 A | 4/1988 | McIntyre |
| 4,762,155 A | 8/1988 | Gruber |
| 4,786,308 A | 11/1988 | Colling |
| 4,875,537 A | 10/1989 | Garnatz et al. |
| 4,895,250 A | 1/1990 | Schifrin |
| 4,921,831 A | 5/1990 | Nakai et al. |
| 4,925,343 A | 5/1990 | Raible |
| 4,963,919 A | 10/1990 | Matsumoto et al. |
| 5,037,690 A | 8/1991 | Van Der Kooy et al. |
| 5,060,598 A | 10/1991 | Richards |
| 5,074,379 A | 12/1991 | Batrice |
| 5,092,457 A | 3/1992 | Islava et al. |
| 5,106,648 A | 4/1992 | Williams et al. |
| 5,180,033 A | 1/1993 | Wilson |
| 5,195,465 A | 3/1993 | Webb et al. |
| 5,215,407 A | 6/1993 | Brelsford |
| 5,218,783 A | 6/1993 | Langezaal |
| 5,300,127 A | 4/1994 | Williams et al. |
| 5,307,577 A | 5/1994 | Werling |
| 5,337,416 A | 8/1994 | Ryan et al. |
| 5,337,496 A | 8/1994 | Glorioso |
| 5,338,131 A | 8/1994 | Bestmann |
| 5,340,642 A | 8/1994 | Baumgartl et al. |
| 5,382,270 A | 1/1995 | Graham et al. |
| 5,404,209 A | 4/1995 | Matsuoka et al. |
| 5,419,945 A | 5/1995 | Lopez |
| 5,422,330 A | 6/1995 | Kaylor et al. |
| 5,424,404 A | 6/1995 | Ruske et al. |
| 5,425,597 A | 6/1995 | Bestmann |
| 5,456,733 A | 10/1995 | Hamilton et al. |
| 5,458,662 A | 10/1995 | Toyone |
| 5,460,765 A | 10/1995 | Derdall et al. |
| 5,477,640 A | 12/1995 | Holtkamp |
| 5,496,378 A | 3/1996 | Hengelsberg et al. |
| 5,516,486 A | 5/1996 | Wright |
| 5,587,277 A | 12/1996 | Yamashita et al. |
| 5,630,377 A | 5/1997 | Kumlin |
| 5,658,571 A | 8/1997 | Gopalan et al. |
| 5,678,954 A | 10/1997 | Bestmann |
| 5,710,190 A | 1/1998 | Jane et al. |
| 5,716,840 A | 2/1998 | Kahler et al. |
| 5,727,499 A | 3/1998 | Armington et al. |
| 5,728,790 A | 3/1998 | Seki et al. |
| 5,747,549 A | 5/1998 | Tsurugai et al. |
| 5,750,661 A | 5/1998 | Schloesser et al. |
| 5,772,721 A | 6/1998 | Kazemzadeh et al. |
| 5,839,674 A | 11/1998 | Ellis |
| 5,840,632 A | 11/1998 | Miller |
| 5,843,203 A | 12/1998 | Lindsay |
| 5,860,391 A | 1/1999 | Maxwell et al. |
| 5,883,025 A | 3/1999 | Karstens et al. |
| 5,922,189 A | 7/1999 | Santos |
| 5,927,049 A | 7/1999 | Simard |
| 5,942,029 A | 8/1999 | Spittle |
| 5,942,457 A | 8/1999 | Santos |
| 5,976,210 A | 11/1999 | Sensibaugh et al. |
| 6,013,524 A | 1/2000 | Friars et al. |
| 6,019,063 A | 2/2000 | Haubensak |
| 6,027,652 A | 2/2000 | Hondroulis et al. |
| 6,032,409 A | 3/2000 | Obonai et al. |
| 6,036,971 A | 3/2000 | Kimoto et al. |
| 6,041,546 A | 3/2000 | Baranova |
| 6,048,968 A | 4/2000 | Etzbach et al. |
| 6,053,125 A | 4/2000 | Kory et al. |
| 6,071,487 A | 6/2000 | Campion et al. |
| 6,076,299 A | 6/2000 | Spittle |
| 6,083,621 A | 7/2000 | Sugimoto et al. |
| 6,085,806 A | 7/2000 | Davis et al. |
| 6,107,242 A | 8/2000 | Ackerman |
| 6,189,260 B1 | 2/2001 | Kusey et al. |
| 6,197,081 B1 | 3/2001 | Schmidt |
| 6,218,321 B1 | 4/2001 | Lorcks et al. |
| 6,219,968 B1 | 4/2001 | Belger |
| 6,271,190 B1 | 8/2001 | Boskamp |
| 6,286,626 B1 | 9/2001 | Evans |
| 6,322,734 B1 | 11/2001 | Zanten |
| 6,357,176 B2 | 3/2002 | Baldwin et al. |
| 6,360,478 B1 | 3/2002 | Spittle |
| 6,391,120 B1 | 5/2002 | Silva |
| 6,395,166 B1 | 5/2002 | Haydock |
| 6,403,124 B1 | 6/2002 | Dottori |
| 6,403,134 B1 | 6/2002 | Nayyar et al. |
| 6,408,568 B1 | 6/2002 | Kusey |
| 6,444,467 B1 | 9/2002 | Fan et al. |
| 6,455,149 B1 | 9/2002 | Hagen et al. |
| 6,472,588 B1 | 10/2002 | Haigler |
| 6,479,433 B1 | 11/2002 | Hann et al. |
| 6,491,840 B1 | 12/2002 | Frankenbach et al. |
| 6,495,058 B1 | 12/2002 | Frankenbach et al. |
| 6,508,306 B1 | 1/2003 | Reddy et al. |
| 6,517,600 B1 | 2/2003 | Dinel |
| 6,539,882 B2 | 4/2003 | Layt |
| 6,547,493 B2 | 4/2003 | Spangler et al. |
| 6,582,637 B1 | 6/2003 | Phinney |
| 6,596,324 B1 | 7/2003 | Homan |
| 6,609,331 B1 | 8/2003 | Stamp |
| 6,620,507 B2 | 9/2003 | Kadowaki et al. |
| 6,624,136 B2 | 9/2003 | Guerin et al. |
| 6,645,392 B2 | 11/2003 | Frankenbach et al. |
| 6,652,766 B1 | 11/2003 | Frankenbach et al. |
| 6,689,609 B1 | 2/2004 | Fan et al. |
| 6,695,544 B2 | 2/2004 | Knudson et al. |
| 6,696,284 B2 | 2/2004 | Haridas |
| 6,709,202 B2 | 3/2004 | Spangler et al. |
| 6,711,850 B2 | 3/2004 | Yelanich et al. |
| 6,732,666 B2 | 5/2004 | Layt |
| 6,773,594 B1 | 8/2004 | van der Wijngaart |
| 6,790,819 B2 | 9/2004 | Trinh et al. |
| 6,793,915 B1 | 9/2004 | Guenin et al. |
| 6,851,221 B2 | 2/2005 | Layt |
| 6,861,131 B2 | 3/2005 | Evans |
| 6,863,027 B1 | 3/2005 | Silva |
| 6,863,816 B2 | 3/2005 | Austin |
| 6,881,338 B2 | 4/2005 | Austin et al. |
| 6,893,193 B2 | 5/2005 | Santha |
| 6,896,805 B2 | 5/2005 | Austin |
| 6,903,197 B2 | 6/2005 | Tresch et al. |
| 6,910,835 B2 | 6/2005 | Spangler et al. |
| 6,913,423 B2 | 7/2005 | Spangler et al. |
| 6,933,371 B2 | 8/2005 | Schroder et al. |
| 6,946,295 B2 | 9/2005 | Polonenko et al. |
| 7,005,410 B2 | 2/2006 | Trinh et al. |
| 7,012,053 B1 | 3/2006 | Barnabas et al. |
| 7,029,586 B2 | 4/2006 | Austin et al. |
| 7,036,272 B2 | 5/2006 | Stoever |
| 7,059,083 B2 | 6/2006 | Abitz et al. |
| 7,087,169 B2 | 8/2006 | Austin |
| 7,091,400 B2 | 8/2006 | Haigler |

| | | |
|---|---|---|
| 7,098,324 B2 | 8/2006 | Haigler et al. |
| 7,109,015 B2 | 9/2006 | Liao |
| 7,117,634 B2 | 10/2006 | Pelton |
| 7,119,166 B2 | 10/2006 | Lin |
| 7,129,289 B2 | 10/2006 | Piret et al. |
| 7,141,659 B2 | 11/2006 | Keeling |
| 7,165,358 B2 | 1/2007 | Wright |
| 7,311,900 B2 | 12/2007 | Conover |
| 7,485,171 B2 | 2/2009 | Lynch et al. |
| 7,488,703 B2 | 2/2009 | Rubin |
| 7,503,143 B2 | 3/2009 | Krysiak et al. |
| 7,587,856 B2 * | 9/2009 | Rubin et al. ............... 47/1.01 R |
| 7,607,258 B2 | 10/2009 | Holmenlund |
| 2001/0013198 A1 | 8/2001 | Krysiak et al. |
| 2001/0030243 A1 | 10/2001 | Hurry et al. |
| 2001/0053545 A1 | 12/2001 | Engwer |
| 2002/0007592 A1 | 1/2002 | Mischo |
| 2002/0011024 A1 | 1/2002 | Baldwin et al. |
| 2002/0041860 A1 | 4/2002 | Requejo |
| 2002/0062770 A1 | 5/2002 | Layt |
| 2002/0073616 A1 | 6/2002 | Pelton |
| 2002/0112293 A1 | 8/2002 | Trinh et al. |
| 2002/0129545 A1 | 9/2002 | Morris |
| 2002/0131826 A1 | 9/2002 | Spangler et al. |
| 2002/0131827 A1 | 9/2002 | Spangler et al. |
| 2002/0194649 A1 | 12/2002 | Fan et al. |
| 2003/0031511 A1 | 2/2003 | Tyler |
| 2003/0061639 A1 | 3/2003 | Polonenko et al. |
| 2003/0065087 A1 | 4/2003 | Nambu et al. |
| 2003/0070191 A1 | 4/2003 | Haigler |
| 2003/0086764 A1 | 5/2003 | Knudson |
| 2003/0089035 A1 | 5/2003 | Courtemanche |
| 2003/0089152 A1 | 5/2003 | Yelanich et al. |
| 2003/0106097 A1 | 6/2003 | Haigler et al. |
| 2003/0140553 A1 | 7/2003 | Moore |
| 2003/0146164 A1 | 8/2003 | Robson et al. |
| 2003/0146405 A1 | 8/2003 | Frankenbach et al. |
| 2003/0157668 A1 | 8/2003 | Polonenko et al. |
| 2003/0172699 A1 | 9/2003 | Phinney |
| 2003/0183140 A1 | 10/2003 | Layt |
| 2003/0209686 A1 | 11/2003 | Frankenbach et al. |
| 2003/0230529 A1 | 12/2003 | Austin et al. |
| 2004/0000517 A1 | 1/2004 | Austin et al. |
| 2004/0005198 A1 | 1/2004 | Spangler et al. |
| 2004/0025422 A1 | 2/2004 | MacQuoid et al. |
| 2004/0040209 A1 | 3/2004 | Layt |
| 2004/0049808 A1 | 3/2004 | Haigler et al. |
| 2004/0049980 A1 | 3/2004 | Principe |
| 2004/0065005 A1 | 4/2004 | Morris |
| 2004/0111967 A1 | 6/2004 | Raap et al. |
| 2004/0141816 A1 | 7/2004 | Spangler et al. |
| 2004/0156687 A1 | 8/2004 | Knudson |
| 2004/0209991 A1 | 10/2004 | Piret et al. |
| 2004/0211721 A1 | 10/2004 | Stamets |
| 2004/0216374 A1 | 11/2004 | Davids |
| 2004/0221397 A1 | 11/2004 | Trinh et al. |
| 2004/0228692 A1 | 11/2004 | McCamy |
| 2004/0237387 A1 | 12/2004 | McCamy |
| 2004/0237388 A1 | 12/2004 | Moore |
| 2005/0034367 A1 | 2/2005 | Morrow et al. |
| 2005/0060811 A1 | 3/2005 | Smith et al. |
| 2005/0061045 A1 | 3/2005 | Lynch |
| 2005/0076564 A1 | 4/2005 | Castleberry |
| 2005/0082222 A1 | 4/2005 | Austin |
| 2005/0098759 A1 | 5/2005 | Frankenbach et al. |
| 2005/0102895 A1 | 5/2005 | Bissonnette |
| 2005/0124065 A1 | 6/2005 | Fan et al. |
| 2005/0141966 A1 | 6/2005 | Greene |
| 2005/0161407 A1 | 7/2005 | McPhillips |
| 2005/0176583 A1 | 8/2005 | Stamets |
| 2005/0183331 A1 | 8/2005 | Kania et al. |
| 2005/0204620 A1 | 9/2005 | Butterfield |
| 2005/0218071 A1 | 10/2005 | Austin et al. |
| 2005/0235558 A1 | 10/2005 | Carrillo |
| 2005/0236315 A1 | 10/2005 | McPhillips |
| 2005/0241231 A1 | 11/2005 | Bissonnette et al. |
| 2005/0246954 A1 | 11/2005 | Bissonnette et al. |
| 2005/0246955 A1 | 11/2005 | Bissonnette et al. |
| 2005/0254899 A1 | 11/2005 | Tyler |
| 2005/0257424 A1 | 11/2005 | Bissonnette et al. |
| 2005/0269260 A1 | 12/2005 | Austin |
| 2005/0274074 A1 | 12/2005 | Stamp |
| 2006/0032804 A1 | 2/2006 | McPhillips |
| 2006/0070294 A1 | 4/2006 | Spittle |
| 2006/0088935 A1 | 4/2006 | Fan et al. |
| 2006/0101881 A1 | 5/2006 | Carin et al. |
| 2006/0107589 A1 | 5/2006 | Rubin |
| 2006/0112629 A1 | 6/2006 | Wright |
| 2006/0160907 A1 | 7/2006 | Stamp |
| 2006/0168881 A1 | 8/2006 | Straumietis |
| 2006/0174379 A1 | 8/2006 | Haigler et al. |
| 2006/0179711 A1 | 8/2006 | Bissonnette et al. |
| 2006/0185235 A1 | 8/2006 | Bono |
| 2006/0207170 A1 | 9/2006 | Smith |
| 2006/0237363 A1 | 10/2006 | Austin et al. |
| 2006/0248796 A1 | 11/2006 | Hashimoto et al. |
| 2007/0022661 A1 | 2/2007 | Slater |
| 2007/0062113 A1 | 3/2007 | Rubin et al. |
| 2007/0094928 A1 | 5/2007 | Hunter |
| 2007/0101644 A1 | 5/2007 | Fujimaru et al. |
| 2007/0209277 A1 | 9/2007 | Schuck et al. |
| 2008/039605 A1 | 2/2008 | Qiu |
| 2008/0155897 A1 | 7/2008 | Van de Wetering et al. |
| 2008/0202024 A1 | 8/2008 | Spittle et al. |
| 2008/0216404 A1 | 9/2008 | Jarvis |
| 2008/0236037 A1 | 10/2008 | Rose et al. |
| 2008/0280760 A1 | 11/2008 | Oliver |
| 2008/0287295 A1 * | 11/2008 | Rubin ........................... 504/100 |
| 2009/0019765 A1 | 1/2009 | Kosinski et al. |
| 2009/0113791 A1 | 5/2009 | Bertin et al. |
| 2009/0139927 A1 | 6/2009 | Kania et al. |
| 2009/0200241 A1 | 8/2009 | Harman et al. |
| 2009/0205249 A1 * | 8/2009 | Rubin ...................... 47/58.1 SC |
| 2009/0249686 A1 | 10/2009 | Pacini et al. |
| 2009/0253576 A1 | 10/2009 | Ikin |
| 2012/0103038 A1 * | 5/2012 | Rubin ............................. 71/23 |

FOREIGN PATENT DOCUMENTS

| | | |
|---|---|---|
| DE | 1145193 B | 3/1963 |
| DE | 10063017 C1 | 7/2002 |
| DE | 102004038299 A1 | 3/2006 |
| EP | 0052526 | 5/1982 |
| EP | 0487655 | 6/1992 |
| EP | 0640280 | 3/1995 |
| EP | 512272 A1 | 8/1995 |
| EP | 0786496 | 7/1997 |
| EP | 849243 A2 | 6/1998 |
| EP | 0867112 | 9/1998 |
| EP | 849243 A3 | 12/1998 |
| EP | 0962129 | 12/1999 |
| EP | 736494 A2 | 8/2001 |
| EP | 1625785 A1 | 2/2006 |
| EP | 2137609 A | 2/2006 |
| FR | 2576745 A1 | 8/1986 |
| GB | 393783 A | 6/1933 |
| GB | 1491940 A | 11/1977 |
| GB | 2272903 A | 6/1994 |
| GB | 2308538 A | 7/1997 |
| GB | 2332353 A | 6/1999 |
| JP | 03280811 A | 12/1991 |
| JP | 10042689 A | 2/1998 |
| JP | 11056017 A | 3/1999 |
| JP | 2002238347 A | 8/2002 |
| KR | 960012590 B | 10/1996 |
| KR | 20020002030 | 1/2002 |
| KR | 20020068556 | 8/2002 |
| KR | 20020085189 | 11/2002 |
| KR | 20020092752 | 12/2002 |
| KR | 10-2003-0003992 | 1/2003 |
| KR | 20030052374 | 6/2003 |
| KR | 20030052375 | 6/2003 |
| KR | 20040062497 | 7/2004 |
| KR | 20040067336 | 7/2004 |
| MX | PA02004768 | 12/2004 |
| NL | 9401955 A | 7/1996 |
| SE | 106170 C1 | 12/1942 |
| WO | 9103149 | 3/1991 |
| WO | 9412576 | 6/1994 |

| WO | 9612687 | 5/1996 |
| WO | 9907943 | 2/1999 |
| WO | 0113706 | 3/2001 |
| WO | 0157156 | 8/2001 |
| WO | 0202889 | 1/2002 |
| WO | 03037069 | 5/2003 |
| WO | 2004037748 A1 | 5/2004 |
| WO | 2004078892 A1 | 9/2004 |
| WO | 2004098270 A1 | 11/2004 |
| WO | 2005070852 A1 | 8/2005 |
| WO | 2005095337 A2 | 10/2005 |
| WO | 2006025657 A1 | 3/2006 |
| WO | 2006055050 A1 | 5/2006 |
| WO | 2007009249 A1 | 1/2007 |
| WO | 2008025027 A2 | 2/2008 |
| WO | 2008048778 A2 | 4/2008 |
| WO | 2008114953 A1 | 9/2008 |
| WO | 2009009805 A1 | 1/2009 |

OTHER PUBLICATIONS

"Facts on Coir: Lessons from the Past" Lanka Santha et al. Landscape Architect and Specifier News magazine Feb. 1999. (5 pgs.).

"Coir Dust a Viable Alternative to Peat Moss" Meerow Alan W. Greenhouse Product News 1997 (6 pgs.).

Meerow, TropicLine Trade Publication, The Potential of Coir (Coconut Mescarp Pith) as a Peal Substitute in Container Media, Tropical Horticulture Newsletter of Ft. Lauderdale Research and Education Center, vol. 6, No. 2 (1993).

Meerow, TropicLine Trade Publication, The Potential of Coir (Coconut Mescarp Pith) as a Peal Substitute in Container Media, Tropical Horticulture Newsletter of Ft. Lauderdale Research and Education Center, vol. 7, No. 3 (1994) (5 pgs.).

Website; www.composters.com GREENCulture Jun. 29, 2010 (2 pgs.).

International Search Report for International Application No. PCTUS0776852, Sep. 9, 2008.

Meerow, Coir Dust, A Viable Alternative to Peat Moss, 1997 (6 pgs.).

Meerow, "Coir Dust (Enviro-Coir), A Viable Alternative to Peat Moss," 2007 (3 pgs.).

Meerow, Coir Coconut Mesocarp Pith (Enviro-Coir) as a Peat Substitute (2007) (5 pgs.).

Nichols, "Coir—a XXIst Century Sustainable Growing Medium," Proceedings of the VIIIth International Symposium on Protected Cultivation in Mild Winter Climates etc., vol. 747 (2006) (1 pg.).

Scoggins, "Development of the Press Extraction Method for Plug Substrate Analysis," 1999 (2 pgs.).

Website: http:www.gpnmag.comCounting-on-Coir-article4388 (2009) (3 pgs.).

Website: http:www.greeneem.comabout.htm (Apr. 2007) (1 pg.).

Website: http:www.greeneem.cmneemcake.htm (Apr. 2007) (1 pg.).

Website: http:www.greeneem.comcococoirpeat.htm (Apr. 2007) (1 pg.).

Website: http:www.rolanka.comindex.asp?pg=coirarticle (1 pg.).

EcoGro: "Nature has Designed the Finest Growing Media for your Plants" (1998).

Martinez, "Coir Could Quickly Gain Share in Growing Media Market," Greenhouse Management & Production, Jul. 1995.

Meerow, "Growth of Two Subtropical Ornamentals Using Coir (coconut mesocarp pith) as a Peat Substitute," HortScience, vol. 29, No. 12 (1994).

Meerow, "Growth of Two Tropical Foliage Plants Using Coir Dust as a Container Medium Amendment," HortTechnology vol. 5, No. 3 (1995).

Stamps et al., "Growth of Dracaena Marginata and Spathiphyllum 'Petite' in Sphagnum Peat-and Coconut Coir Dust-based Growin Media," Journal of Environmental Horticulture, vol. 17, pp. 49-52 (1999).

Viswanathan et al., "Pressure Density Relationships and Stress Relaxation Characteristics of Coir Pith," Journal of Agricultural Engineering Research, 73(3) 217 (1999).

http://www.emilysplants.com/My_store_pages/ezsoilpottingsoil.html (1 pg).

The Scotts Company LLC's Invalidity Contentions Pursuant to Patent Rule 3.3 in the United States District Court for the District of Nevada, Case No: 09-CV-02419 (GMN) RJJ, dated Dec. 13, 2010 (40 pgs.).

* cited by examiner

COMPRESSED GROWING MEDIUM

RELATED APPLICATIONS

This application is a continuation application of U.S. patent application Ser. No. 12/368,216 filed Feb. 9, 2009, which application was a divisional of U.S. patent application Ser. No. 10/993,599 filed Nov. 19, 2004, both entitled "COMPRESSED GROWING MEDIUM," which applications are incorporated herein in their entireties.

BACKGROUND

Pre-seeded soil mixtures, such as germinating mixes, potting soils, peat cubes and compressed pellets, have been used in forestry, agricultural, commercial and home uses. These mixtures contain seeds dispersed in a soil mixture that is later deposited to allow the seeds to germinate and grow. These mixtures thus obviate time-consuming labor, such as digging, tilling and cultivating. Some mixtures are also used in indoor and outdoor pots and planters. Most soil mixtures are usually free from insects, diseases and weeds and have enough fertilizer incorporated for the first few weeks of plant growth. However, because of the favorable environment provided by the soil mixtures the seeds tend to germinate during storage or transport of the soil mixture before the mixture is deposited for its intended use. The seedlings are bulky and often become root-bound, resulting in limited time periods for storage and transportation. They are also exposed to injury and to unfavorable environmental conditions, resulting in excessively high mortality rates of the seedlings.

In order to prevent easy germination and seed mortality, soil mixtures have been compressed into soil wafers or pellets to provide easy modes of transporting the soil mixtures while limiting the water necessary for germination. However, these compressed wafers may not effectively prevent water intrusion or germination of the seeds.

SUMMARY

A growing medium includes a bulking agent and a water-retentive polymer blended together and compressed at a volume-to-volume ratio ranging from about 2:1 to about 10:1, preferably from about 5:1 to about 10:1, and more preferably from about 7:1 to about 8:1, and being substantially free of a water-soluble binder material.

BRIEF DESCRIPTION OF THE DRAWINGS

The accompanying drawings illustrate various embodiments of the present system and method and are a part of the specification. The illustrated embodiments are merely examples of the present system and method and do not limit the scope thereof.

Throughout the drawings, identical reference numbers designate similar, but not necessarily identical, elements.

DETAILED DESCRIPTION

Figure 1:
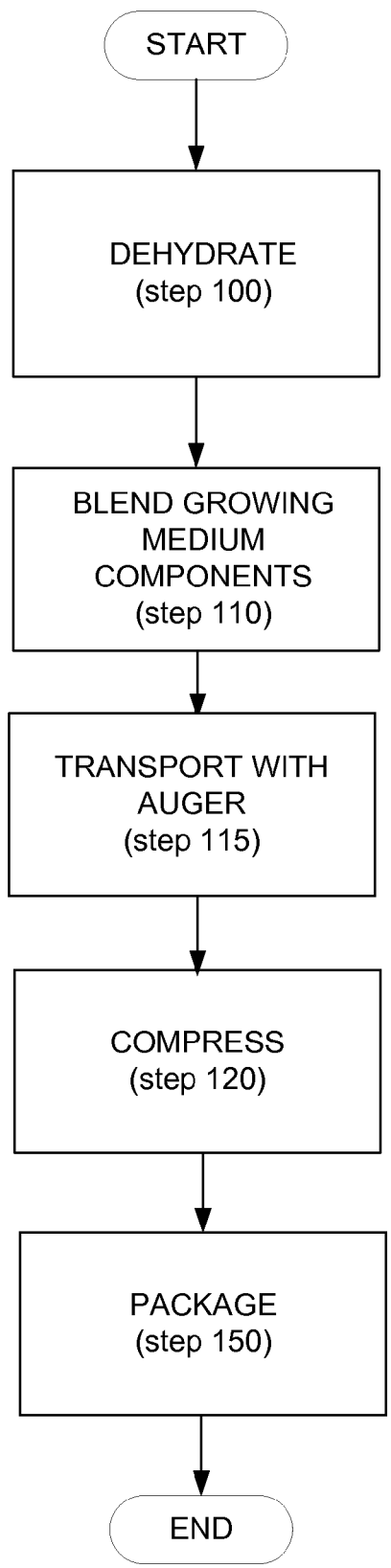
FIG. 1 is a flow diagram depicting an exemplary embodiment of a method of making a compressed soil mixture.

An exemplary system and method for implementing a compressed growing medium with reduced seed germination is disclosed herein. More specifically, a compressed growing medium is disclosed that contains a water-retentive polymer, but contains no binder material, such as polyvinyl alcohol (PVA). Numerous specific details are set forth for purposes of explanation and to provide a thorough understanding of the present system and method for implementing a compressed growing medium. It will be apparent, however, to one skilled in the art, that the present products and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

According to one exemplary embodiment, the growing medium comprises a bulking agent in combination with a water retentive polymer and other components as described below.

A hydrophilic fibrous bulking agent forms the majority of the growing medium. Generally, the bulking agent ranges from about 50% to about 98% of the growing medium. Examples of the bulking agent include coir, peat, cotton, mineral wool, paper pulp, peat bark, birch bark, wool and/or hair. In one embodiment the bulking agent comprises coir dust with a small amount of short to medium length coir fibers, and possibly other parts of the coconut that might enhance drainage and growth. Coir fibers assist in drainage of water while the coir dust enhances the expansion of the growing medium.

The bulking agent used in the growing medium is also dehydrated, having a moisture of content of about 20% or less, and preferably of about 18% or less, and more preferably of about 11% or less. Using a dehydrated bulking agent helps maintain the potency of all growing medium components, including fertilizers and seeds. Using a dehydrated bulking agent in a pre-seeded growing medium also enhances the ability of the seeds to live longer. It is understood that climatic conditions after production may affect the moisture content and appropriate packaging may be required to prevent this while the growing medium is in storage or transit.

The bulking agent that is used in the growing medium is also a low-compressed bulking agent. By using a low-compressed bulking agent the speed of dehydration and expansion of the growing medium is increased, and the expanded volume of the growing medium is usually equal to or greater than its volume before it is dehydrated and compressed. The dehydrated, low-compressed bulking agent also maintains the growing medium substantially free from all insects, diseases and weeds. A low compressed bulking agent is an bulking agent that has been compressed at a volume-to-volume ratio of not more than about 3:1. Thus, in some instances it may be necessary to decompress compressed coir to a volume-to-volume ratio of about 3:1 or less.

The grind size of the bulking agent helps to control the structural integrity of the growing medium even when wet, and also affects the expansion process. Generally, the grind size of the bulking agent depends on various factors of the growing medium, such as its size in compressed form, the size and type of any seeds included in the growing medium, and the amount of water drainage needed. Thus, the grind size is influenced by the location of use of the growing medium since the atmospheric conditions of locations vary from arid to humid, and since different climate zones support different types of seeds. Generally, the bulking agent grind size range from being able to pass through an approximately ⅛ inch mesh screen to being able to pass through an approximately 1 inch mesh screen.

The bulking agent may also include any added natural porous substrate that enhances the bulking agent, such as by adding beneficial nutrients or improving water drainage. Examples of suitable natural porous substrates include, but are not limited to, pine bark, fir bark, redwood bark, hardwood bark, polystyrene foam, sawdust, rock wool, perlite, vermiculite, scoria, composted organic materials, shale rock, calcined clay pellets and volcanic pumice. These porous substrates enhance the rate of water percolation or drainage pulled by gravity and the quantity of water stored after drainage.

The growing medium also includes one or more water-retentive polymers. These polymers, also called superabsorbing polymers (SAP's), are hydrophobic materials that can absorb fluid and retain it under pressure without dissolution in the fluid being absorbed. The materials used are generally all synthesized by one of two routes. In the first, a water soluble polymer is cross-linked so that it can swell between cross-links but not dissolve. In the second, a water-soluble monomer is co-polymerized with a water-insoluble monomer into blocks. Generally, the water-retentive polymer is a non-foamed polymer. Suitable water-retentive polymers include, but are not limited to, saponified starch graft polyacrylonitrile copolymers, polyacrylic acid, polymalsia anhydride-vinyl monomer superabsorbents, starch-polyacrylic acid grafts, polyacrylonitrile based polymers, cross-linked polyacrylamide, cross-linked sulfonated polystyrene, cross-linked n-vinyl pyrrolidone or vinyl pyrrolidone-acrylamide copolymer, and polyvinyl alcohol superabsorbents. These polymers absorb many times their own weight in aqueous fluid. Additional suitable water-retentive polymers include, but are not limited to sodium propionate-acrylamide, poly(vinyl pyridine), polyethylene imine, polyphosphates, poly(ethylene oxide), vinyl alcohol copolymer with acrylamide, and vinyl alcohol copolymer with acrylic acid acrylate. Combinations of the above polymers may also be used, depending on the intended use of the growing medium, and the desired absorption and release rates of water and nutrients.

In one exemplary embodiment the water-retentive polymer is a potassium- or sodium-based polymer, such as a synthetic polyacrylate/polyacrylamide copolymer. Like many absorbent polymers, it can absorb many hundred times its weight in water. In an embodiment, the absorbent polymer is acrylamide/potassium acrylate copolymer. Potassium-based polymers are non-toxic and do not cause harm to the environment. Additionally, potassium is a nutrient that promotes plant development. Generally, the water-retentive polymer used ranges up to about 25% by dry weight of potassium acrylate acrylamide copolymer, more preferably in an amount from about 2% to about 15% by dry weight of the growing medium.

The growing medium may also include a non-ionic surfactant or emulsifier that wets the dry hydrophilic bulking agent and decreases surface tension that would otherwise prevent water take up. Thus, the surfactant increases the rate at which the bulking agent absorbs water. Suitable surfactants include, but are not limited to polyoxypropylene-polyoxyethylene block co-polymers; alkanol amides, betamol derivatives; block co-polymers comprising a series of condensates of ethylene oxide with hydrophobic bases formed by condensing propylene oxide with proylene glycol; ethyoxylated compounds comprising alcohols, alkyl phenols, amines and amides, alkylphenol ethoxylates, fatty alcohol polyglycol ethers, oxo-alcohol polyethylene glycol ethers, alkylphenol-ethoxylates, fatty or oxo-alcohol polyethylene glyco ethers, and hydrophilic and hydrophobic block copolymers. In one embodiment the non-ionic surfactant is polyoxypropylene-polyoxyethylene block copolymer in an amount from about 0.001% to about 3.5% by dry weight of the total matrix.

The growing medium is also free of a water soluble binder material. Conventional growing media having a water-retentive polymer also contain a water soluble binder material, such as polyvinyl alcohol (PVA), polyvinyl acetate or a polyacrylate, to bind a growing medium together when wet and help to maintain the structural integrity of the growing medium. However, the compressed growing medium described herein does not require a binder material to maintain its structural integrity, and thus contains no PVA or other binder material.

The growing medium may also contain various other components. In one embodiment, the compressed growing medium includes seeds, thereby forming a pre-seeded compressed growing medium. The pre-seeded, compressed growing medium protects seeds against injury and enhances the conditions for germination and growth of seeds and plants. When wetted, the growing medium yields a gel that can bond to a growing surface, such as ground soil, localizing the seedling to grow at that point and binding the growing medium to the roots.

A pre-seeded, compressed growing medium typically uses a water retentive polymer that has a water absorbtivity from about 50 to about 600 times its weight. At such absorption levels, the entire composition upon exposure to rainfall or watering is converted to a wet, gas-permeable gel that protects and bonds the seed to the ground during germination.

The compressed growing medium may also contain a fertilizer. The majority of the added fertilizer is in water-insoluble granular form, and may be either organic or inorganic. The fertilizer also usually does not inhibit the water absorption or release functions of the water-retentive polymer. The specific fertilizer used in the compressed soil is specifically targeted to a particular plant or plants and geographical region, since different regions and plants can be benefited by different fertilizers. The fertilizer is preferably configured and chosen to contain nutrients that are effective for up to about 8 weeks. Examples of suitable fertilizers include, but are not limited to, manures, bone meals, blood meals, cottonseed meal, fish emulsion, sewage sludge, compost, urea, ureaform, isobutylidene diurea, slow-release fertilizers, sulfur-coated urea, oxamide, melamine, calcium nitrate, ammonium bicarbonate, nitrate of soda, calcium cyanamide, ammonium sulphate (sulphate of ammonia), calcium ammonium nitrate (limestone ammonium nitrate), ammonium chloride, ammonium sulphate nitrate, nitrogen solutions, ammonium nitrate, anhydrous ammonia, basic slag, single superphosphate, rock phosphate (raw), dicalcium phosphate, triple superphosphate, kainit, potassium magnesium sulphate (sulphate of potash magnesia), potassium chloride (muriate of potash), potassium sulphate (sulphate of potash), mono (di)-ammonium phosphate, ammoniated superphosphates, ammoniated polyphosphates, nitrophosphates, potassium nitrate, potassic slag, potassic superphosphates, compound fertilizers, complex fertilizers, mixed fertilizers, bulk blend and combinations thereof.

The compressed growing medium may also contain other components, such as nutrients, pesticides, insecticides, fungicides, plant growth enhancers, or other beneficial components known to those of skill in the art. These components are absorbed, stored and released by the water-retentive polymer(s) on a consistent level as needed by the plants.

FIG. 1 depicts an exemplary method of making a compressed growing medium, both pre-seeded and non-seeded. The coir and/or other bulking agents are first dehydrated to about 20% moisture content or less in an air circulating oven set to approximately 95° C. (step 100). Preferably, the bulking agent is dehydrated to 18% or less humidity, and more preferably to about 11% or less humidity. If necessary, the bulking agent is also decompressed to a volume-to-volume ratio of about 3:1 or less. The growing medium components, including the bulking agent, the water-retentive polymer and any other additional components, are then blended together with a blender or other mixer (step 110). The mixture is then transported by an auger (screw type conveyer) to a hopper that feeds a press (step 115). The auger takes air out of the mixture and keeps the mixture blended, which could separate if left standing for a period of time.

The growing medium, whether pre-seeded or non-seeded, is then compressed at a volume-to-volume ratio ranging from about 2:1 to about 10:1 in order to provide a compressed growing medium suitable for packaging, shipment and sale (step 120). Preferably the growing medium is compressed at a volume-to-volume ratio ranging from about 5:1 to about 10:1, and more preferably from about 7:1 to about 8:1. The growing medium is typically compressed into bricks, slabs, wafers, pellets, cubes, triangles and any other shape. If the compressed growing medium includes seeds, its size and shape may be determined by the size of the included seeds and what is necessary to protect those seeds during compression. The terms "wafer" and "pellet" as used herein are not limited to any one shape, but may include shapes that are spherical, elliptical, egg-shaped, square, rectangular, crescent, convex, concave, flat or any other regular or irregular shape. The compressed bricks, slabs, wafers and pellets may then be packaged in pouches, grow-bags, cans, canisters, jars, boxes, and other packages known to those of skill in the art (step 150). The compressed soil, if containing seeds, is then vacuum packed to keep the environment dry and consistent to increase seed life longevity.

Figure 2A:
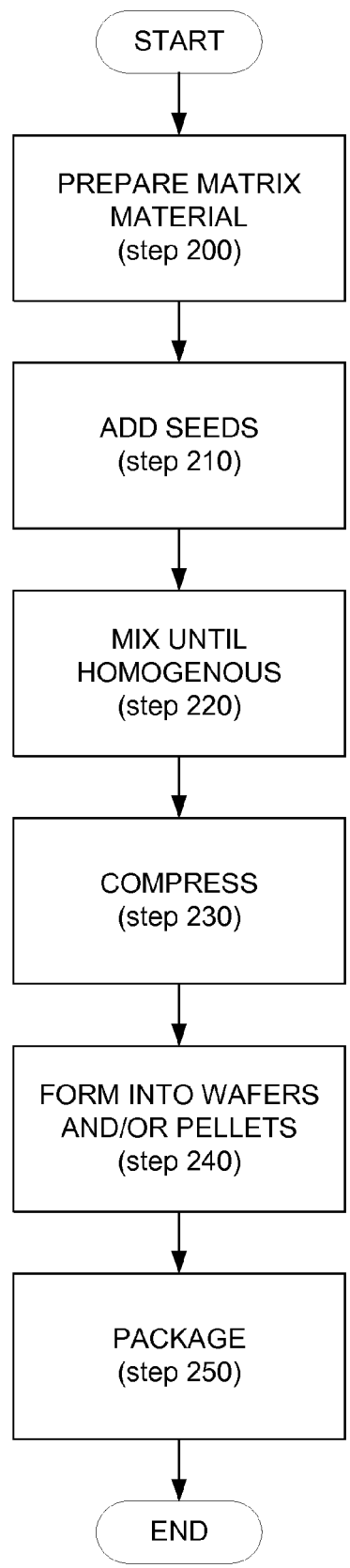
FIG. 2a is a flow diagram depicting another exemplary embodiment of a method of making a compressed soil mixture.
Figure 2B:
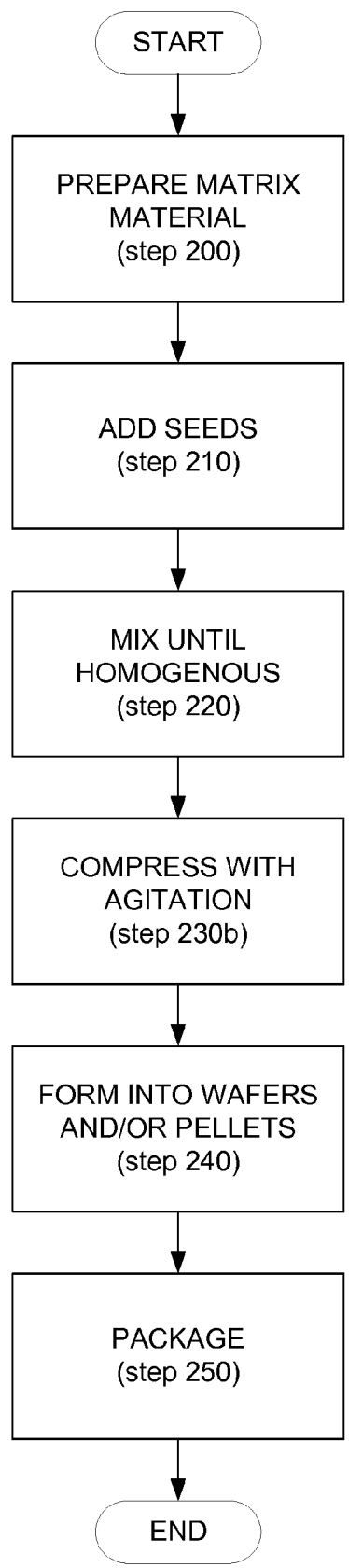
FIG. 2b is a flow diagram depicting another exemplary embodiment of a method of making a compressed soil mixture.
Figure 3:
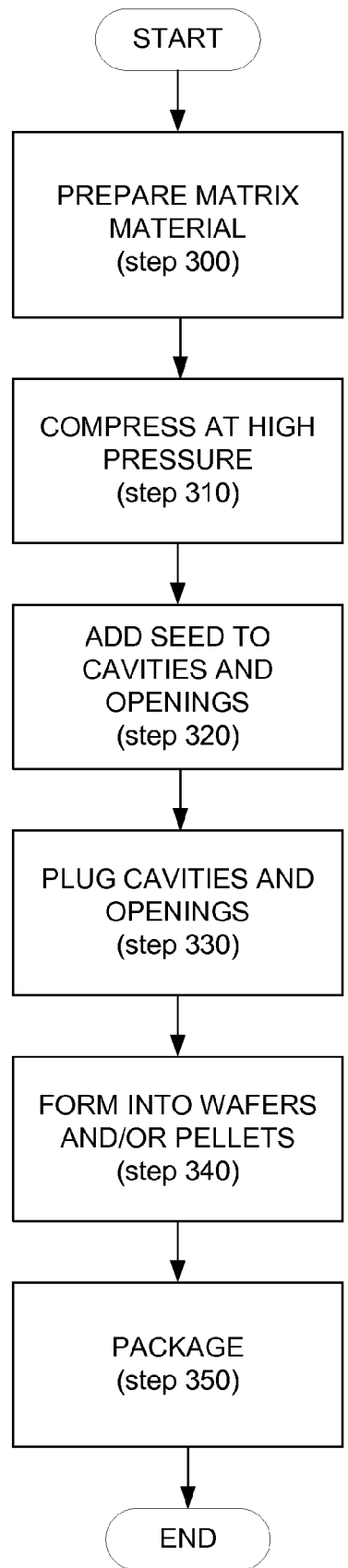
FIG. 3 is a flow diagram depicting another exemplary embodiment of a method of making a compressed soil mixture.
Figure 4:
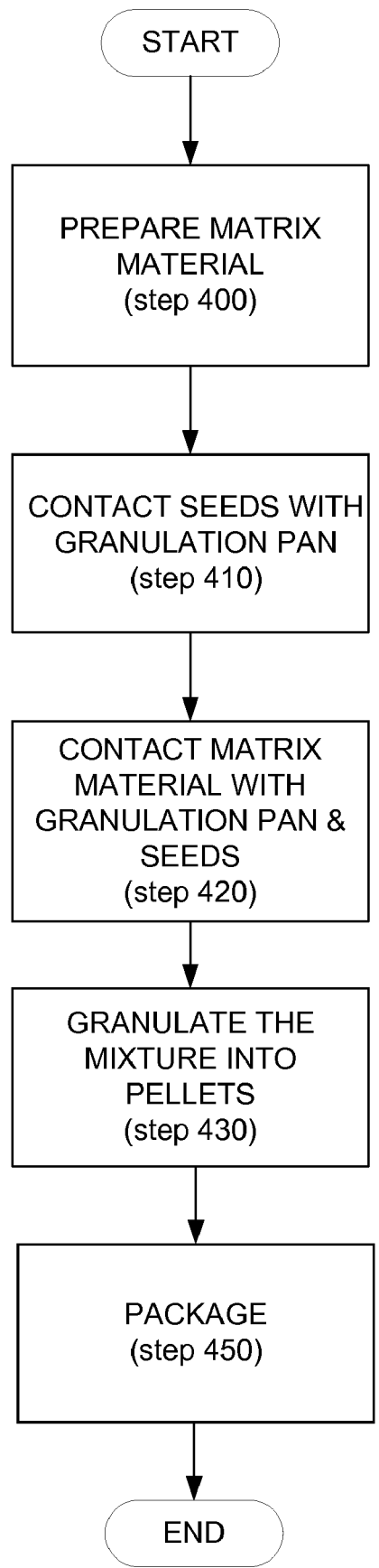
FIG. 4 is a flow diagram depicting another exemplary embodiment of a method of making a compressed soil mixture.

FIGS. 2-4 depict various embodiments of methods of making pre-seeded, compressed growing medium wafers and pellets. In one embodiment, as shown in FIG. 2, pre-seeded, compressed wafers and pellets are made by first blending together the growing medium components (step 200) in the manner described above. Seeds are then added to this medium (step 210), which is then blended together by means of a mixing apparatus so as to produce a homogenous, or substantially homogenous, pre-seeded growing medium (step 220). The seeded mixture is then compressed at about room temperature to form a pre-seeded, compressed growing medium (step 230). The compression can be carried out by means of a pressing device, such as a compactor or two form cylinders rotating in opposite directions. If the growing medium is compressed while containing the seed, a lower pressure may be used to prevent injury to the seed. The pressure or tonnage used varies depending on the seed size and the compressed shape that particular seed needs, and is usually at about the maximum pressure possible that does not injure the seed(s) embedded in the mixture). In one embodiment, shown in FIG. 2b, the growing medium is compressed with concurrent agitation, such as by an auger, in order to thoroughly mix all components of the growing medium and prevent settling of heavier components, such as the water-retentive polymers, fertilizers and seeds (step 230b). The pre-seeded, compressed growing medium may then be molded, shaped or formed into wafers and/or pellets (step 240). The wafers and/or pellets are then packaged to reduce germination (step 250), as will be described in further detail below.

In another embodiment, as shown in FIG. 3, a pre-seeded, compressed growing medium wafer is made by first preparing a growing medium from the above-described components (step 300). This growing medium is then pressed at high pressures (approximately 7500 psi) (step 310) before the seed is added to the growing medium (step 320). The pressure usually varies, depending on the shape of the compressed growing medium and whether it includes seeds or not. If the size of the compressed growing medium is small, any seeds are typically mixed in to the growing medium before compression. For larger compressed growing medium configurations, such as bricks, slabs or cubes the seed is added after the compression. The size of the cavity to hold the seed is determined by the size of the particular seed type used. Once the seed is placed in the cavity, the cavity opening is plugged (step 330) with a suitable material that will remain in place once dried and that is not toxic to the seed or germinating plant. In one embodiment the growing medium cavities are plugged with a paste composed of 50% by dry weight dry peat and 50% by dry weight of an aqueous solution containing 11.25% by dry weight PVA and 0.125% by dry weight nonionic surfactant. Other materials may be used to plug the seed cavity, such as silicate clays. The compressed growing medium is then formed into wafers and pellets (step 340) and then packaged for sale (step 350).

In any method used, since heat may be released during the pressing process it may be necessary to design the pressing device and to carry out the pressing process in a manner to keep the temperature of the different constituents of the wafers or pellets, and in particular the temperature of the grains of seed contained therein, from exceeding 35° C., and preferably from exceeding 30° C., so that the germinating ability of the grains of seed will not be negatively affected. After the wafers or pellets have been pressed, or possibly while they are being pressed, they may be cooled down again to normal room temperature of about 20° C. to 25° C., such as by passing an air stream through them or by exposing them to ambient temperature.

In another embodiment, shown in FIG. 4, compressed seed pellets are formed by first preparing a growing medium (step 400). A source of agronomic seeds are then contacted with a granulation pan (step 410). The growing medium is then contacted with the granulation pan (step 420) and the mixture is granulated (step 430) in the granulation pan to form pellets of encapsulated agronomic seeds. The compressed seed pellets may then be packaged (step 450), as described below.

Other methods for forming compressed pellets include spraying seeds while rotating in a mixer, the use of drum coaters, fluidized bed techniques, Wurster air suspension coating processes, pan coaters and spouted beds. In each of these methods the seeds may be presized prior to coating.

Figure 5:
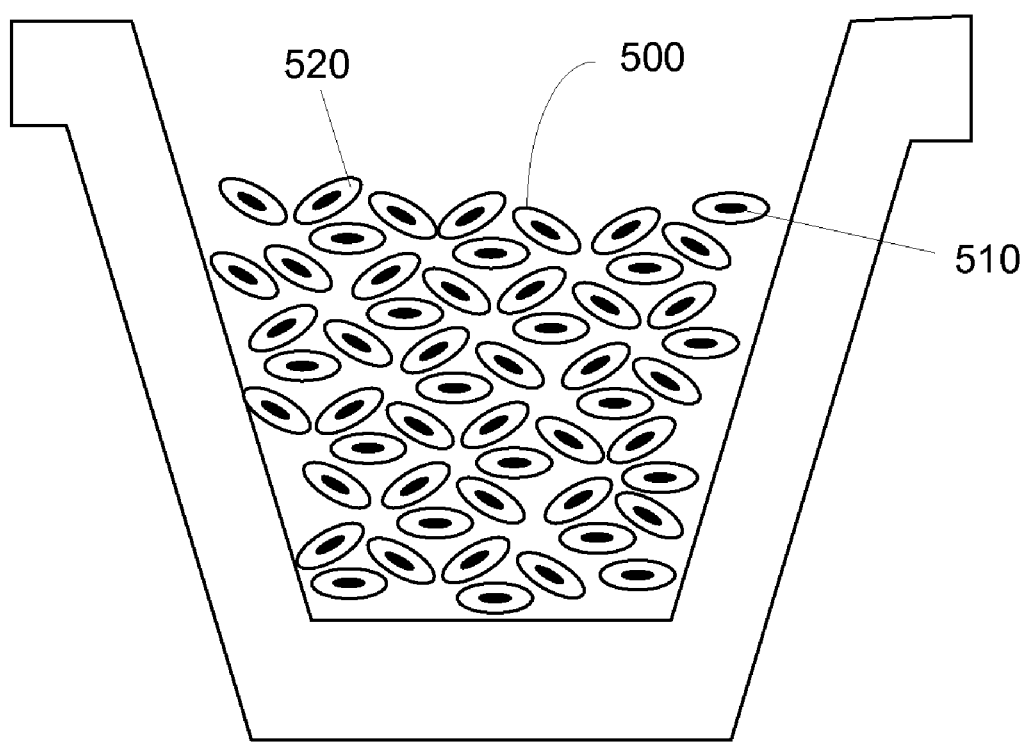
FIG. 5 depicts one exemplary embodiment of a compressed soil pellet mixture.
Figure 6:
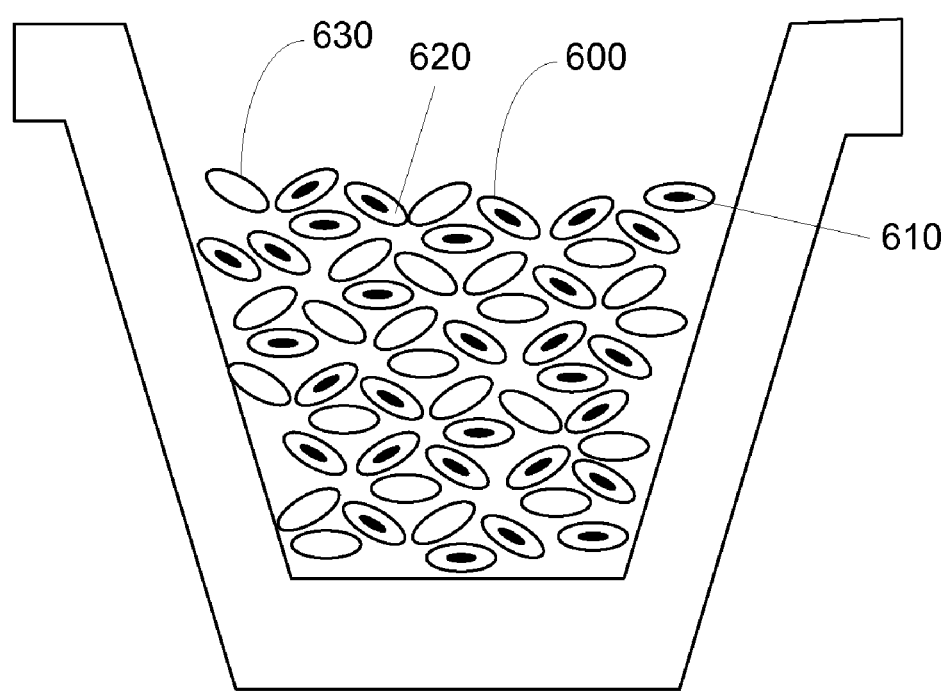
FIG. 6 depicts another exemplary embodiment of a compressed soil pellet mixture.
Figure 7:
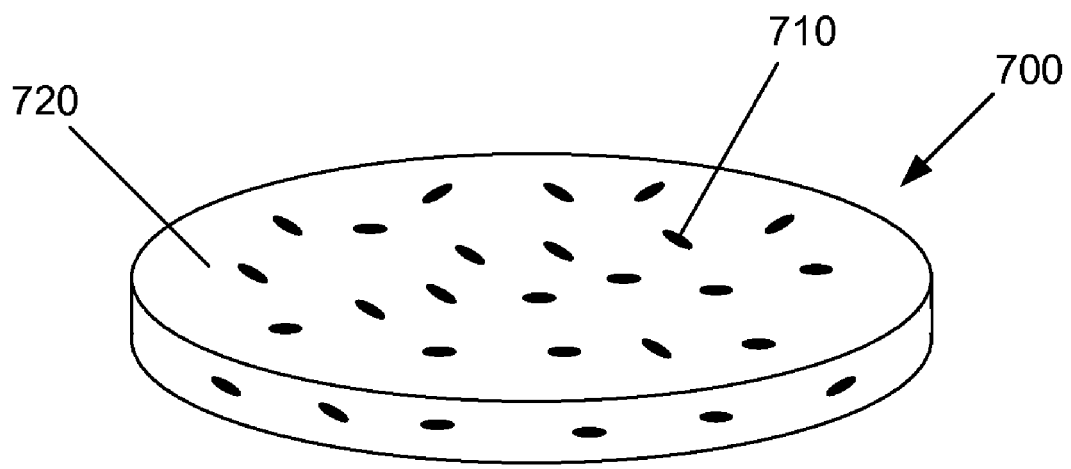
FIG. 7 depicts an exemplary embodiment of a compressed soil wafer.

As shown in FIGS. 5-7, the pre-seeded compressed growing medium wafers (700) and pellets (500, 600) generally contain seeds (510, 610, 710) uniformly dispersed throughout the soil mixture (520, 620, 720). The seeds used in the growing medium (510, 610, 710) may include, but are not limited to, seeds for vegetables, flowers, trees, grasses, herbs, grains, crops, and other plants. The wafers (700) and pellets (500, 600) each contain at least one grain of seed, but may contain, depending on the type and size of the grains of seed, at least 2, preferably at least 4 or up to not more than 15 grains of seed. The grains of seed (510, 610, 710) are generally distributed uniformly over the entire volume of the wafers or pellets. In one embodiment the wafers (700) and pellets (500, 600) contain a variety or mixture of any of the above seeds. In one embodiment, shown in FIG. 4, the growing medium includes compressed pellets (500) in which each pellet (500) includes a seed (510), such as grass seeds, encapsulated in the growing medium (520). This embodiment is particularly useful in creating large, grassy areas such as in sports arenas, parks and playing fields. In a further embodiment, shown in FIG. 6, some of the compressed pellets (600) include seeds (610) encapsulated in the growing medium (620) while other pellets (630) contain a growing medium (620), but have no seeds.

As illustrated in the exemplary methods mentioned above, the pre-seeded, compressed growing medium wafers and pellets can be packaged to minimize and reduce germination of the seeds during storage and transport. (steps 150, 250, 350, 450) Since many factors contribute to seed germination, such as seed viability, ambient moisture, proper temperature, ample oxygen, and light, many methods are available to alter these factors to reduce seed germination during storage and transport. Maintaining humidity and/or oxygen levels at the lowest possible levels in the packaging is an efficient way of reducing premature seed germination and increasing the longevity of seed life before germination. Suitable methods for producing a dehydrated packaging include vacuum-packing, pillow packing, controlled atmosphere packing, modified atmosphere packing, desiccant packing, and other methods known to those of skill in the art.

In one embodiment the pre-seeded, compressed growing medium wafers and pellets are vacuum-packed. Vacuum packing is a process whereby air and/or the water in it are evacuated from a storage bag or container, thus decreasing the oxygen content and humidity in and around the soil mixture. Generally, the vacuum-packing process may be carried out by any process or apparatus known to those of skill in the art. Conventional vacuum-sealing or vacuum-packing machinery may be used, such as external clamp pouch machines, external clamp snorkel machines (also known as retractable nozzle machines) and chamber machines.

In other embodiment the wafers and pellets are packaged by pillow packing, controlled atmosphere packing or modified atmosphere packing. In these methods, after the growing medium is vacuum-packaged a gas or combination of gases is injected into the package to yield a package that has substantially all atmospheric oxygen removed but is not drawn down tight around the growing medium. Suitable gases include, but are not limited to nitrogen, carbon monoxide, carbon dioxide, sulfur dioxide, and inert gases such as helium, argon, xenon and neon. The added gas or gases reduces the pressure generated by the package on the growing medium and seeds. These anoxic packages contain little to no oxygen, thus greatly inhibiting seed germination while permitting a higher moisture content to help maintain the integrity of the growing medium structure. In another embodiment, the compressed growing medium is vacuum freeze dried before packing.

In yet another embodiment, the growing medium is packaged with a desiccant to reduce the ambient humidity. Suitable desiccants include, but are not limited to, silica gel, clays, calcium oxide, calcium sulfate, calcium chloride, molecular sieves, charcoal, alumina, alumino silicate, calcium fluoride, lithium chloride, starches, a zeolite, barium oxide, magnesium perchlorate, glycerin, calcium hydride, phosphoric anhydride, phosphoric acid, potassium hydroxide, sulfuric acid, ethylene glycol, barium oxide, sodium sulfate and combinations thereof. In another embodiment, inert gas may also be introduced into the package to replace air and/or moisture. Including a desiccant or inert gas significantly reduces humidity, thus greatly reducing seed germination.

The packages used for packaging the growing medium according to the above methods include, but are not limited to jars, cans, plastic pouches, standard flat vacuum pouches, and other packages known to those of skill in the art. In one embodiment the package comprises vacuum pouches made of multi-layered nylon and polyethylene. In another embodiment the package comprises plastic cans such as tennis ball cans. Since the vacuum-packing and other methods of packing described above are used to produce substantially dehydrated and anoxic packages for reduced seed germination, other methods of packing known to those of skill in the art that do not reduce humidity or oxygen content can be used for a compressed growing medium that is not pre-seeded.

Figure 8:
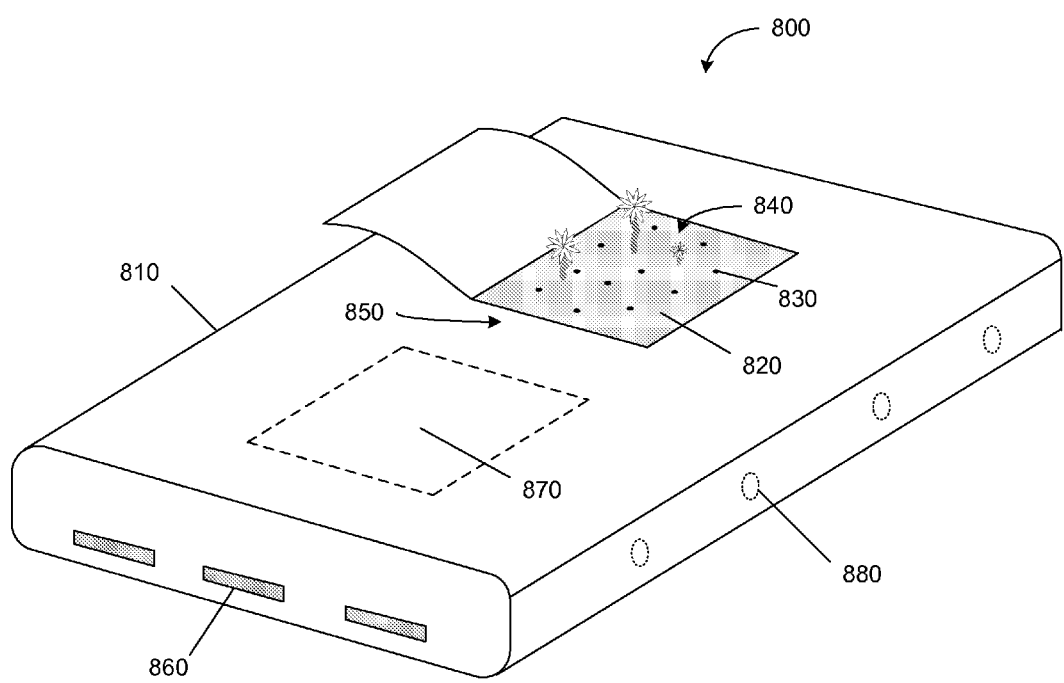
FIG. 8 depicts an exemplary embodiment of a grow bag.

In another embodiment, shown in FIG. 8, the compressed growing medium is packaged in a grow bag (800). The grow bag (800) generally includes a sealed plastic bag (810) that contains a compressed growing medium (820) inside, typically in a brick or slab form. The compressed bricks or slabs can range up to about 6 lbs, and are typically packaged in the plastic bag by vacuum-packing or other methods as described above that maintain the appropriate atmospheric conditions for reduced seed germination and enhanced seed longevity. The compressed growing medium (820) can also contain seeds (830) if it is a pre-seeded growing medium. The pre-seeded growing medium allows a user to just add water to begin the germination process. The plastic bag (810) is usually made from a breathable plastic, such as co-extruded polyethylene, polypropylene. The plastic used may also be configured to be rot-resistant, UV resistant, and/or weather resistant. The grow bag (800) obviates the need for a planter or pot because plants (840) can be planted in the grow bag (800) by cutting a hole (850) in the plastic bag (810) and planting in the exposed growing medium (820). Grow bags of this type are commonly used in horticulture and hydrophonic green house industries for growing strawberries, tomatoes, peppers, cucumbers, and are also used in the floriculture industry for roses, gerbera and many more highly demanded seasonal and non-seasonal flowers.

The grow bag provides many benefits over traditional grow bags or growing media. Since the growing medium (820) used in the grow bag (800) contains a water-retentive polymer, the need for drainage holes can be eliminated since the polymer retains most of the moisture. The grow bags (800) also are easy to transport and take up little space since the growing medium (820) is compressed. When wetted, the growing medium expands and provides an enhanced growing environment for plants. Plants (840) grown in the grow bag (800) quickly develop more elaborate and stronger root systems and have significantly reduced root diseases (recent studies strongly suggest coir inhibits Pithium and Phytothora growth). The grow bags (800) are also recyclable and easy to handle or dispose.

The grow bag (800) may be fluted with pre-punched drain holes (860). The grow bag may also contain perforated sections (870) that can be manually torn and removed to expose the growing medium (820) for planting or to expose the growing medium (820) to improve aeration and access to sunlight and to remove the plastic bag (810) as a barrier to plant and seedling growth. Other drainage perforated sections (880) can be removed to provide water drainage holes. The plastic bag may also be printed with instructions where to pierce the bag, where the seeds have been placed, where seeds are to be placed and where the other materials such as the nutrients and polymers have been equally dispersed in the growing medium.

Generally, the compressed growing medium, whether in bricks, slabs, wafers and pellets, cubes or other shapes can be used anywhere a conventional soil or growing medium is used, including sports fields, parks, home lawns, gardens, indoor pots, outdoor pots, greenhouses, nurseries, farms, forests, and other agricultural, forest, commercial and home uses. By compressing the growing medium and packaging it to reduce germination, the seeds in the soil mixture live longer, thereby producing a higher quality product when it is deposited for its intended use. The compressed, packaged growing medium is also easier to transport and handle, being roughly 10% of the weight or a traditional planting medium.

The wafers and pellets can be deposited according to any method known to those of skill in the art, such as by hand or with machinery. After depositing the wafers and pellets, water is added to the soil mixture. When the soil mixture is wetted it becomes gel-like, expands, and bonds to the soil localizing the seedling's growth at the point the seed capsule is deposited. Approximately one inch of rain is required to activate the preferred capsule matrix; however, water requirements can be varied in light of local climate conditions, seed requirements, and resulting proportions of matrix components. The resulting gel-like structure permits the exchange of oxygen and the retention of water that are essential for the germination of the seeds. It also forms a mechanical barrier to predators. In addition, the encapsulating process permits the optional inclusion of nutrients, fertilizers and fungicides selected to address local conditions. In other embodiments the soil mixture includes commercial fungicides such as Banlate™ at levels to 5000 ppm, Ridamil™ at levels to 50 ppm, and Thiaram™ at levels up to 25 ppm without toxic effect to the seeds, the polymers or the nutrients that might be added.

Precise ratios of ingredients affect the most advantageous characteristics of the growing medium. The particular use made of the growing medium and local growing conditions will dictate the ratios chosen. Generally the growing medium, when wetted, holds sufficient water to supply the needs of the germinating seeds, bedding plant, or house plant, but not hold so much to subject the seed or plant to a deleterious amount of water. The combination of component characteristics in the growing medium yields a product that has qualities of performance, convenience and cost-effectiveness.

The preceding description has been presented only to illustrate and describe exemplary embodiments of the present system and method. It is not intended to be exhaustive or to limit the system and method to any precise form disclosed. Many modifications and variations are possible in light of the above teaching. It is intended that the scope of the system and method be defined by the following claims.

What is claimed is:
1. A method of making a growing medium, comprising:
blending a dehydrated bulking agent, including coir, and a non-ionic surfactant or emulsifier; and
compressing said dehydrated bulking agent, including coir, and said non-ionic surfactant or emulsifier at a volume-to-volume ratio ranging from about 3:1 to about 10:1;
wherein said compressed growing medium is not hydrophobic and maintains a compressed shape without a water soluble binder until hydrated.
2. The method of claim 1, wherein said dehydrated bulking agent comprises less than 20% moisture content.
3. The method of claim 1, wherein said dehydrated bulking agent is compressed at a volume-to-volume ratio between 1:1 and 3:1 prior to said blending with said non-ionic surfactant or emulsifier.
4. The method of claim 1, further comprising:
forming said growing medium into a wafer, pellet, brick, slab, cube or triangle.
5. The method of claim 1, further comprising adding a fertilizer, nutrients, a pesticide, an insecticide, or a fungicide to said growing medium.
6. The method of claim 1, wherein said compressing further includes agitating said growing medium prior to said compression.
7. The method of claim 1, further comprising cooling said growing medium to between 20° C. and 25° C. during said compression of said dehydrated bulking agent.
8. The method of claim 1, wherein said growing medium is maintained below about 35° C. during said formation of said growing medium.
9. The method of claim 1, further comprising forming said compressed growing medium into an irregular shape.
10. The method of claim 1, further comprising adding seeds to said compressed growing medium.
11. A method of making a growing medium, comprising:
dehydrating a ground coir bulking agent having a grind size between ⅛ inch mesh and 1 inch mesh to less than 20% moisture content;
adding a non-ionic surfactant or emulsifier to said dehydrated ground coir bulking agent;
compressing said bulking agent and said non-ionic surfactant or emulsifier at a volume-to-volume ratio ranging from about 5:1 to about 10:1;
wherein said compressed bulking agent and non-ionic surfactant or emulsifier is free of a water soluble binder; and
wherein said compressed bulking agent and non-ionic surfactant or emulsifier is maintained below about 35° C. during said formation of said growing medium.
12. The method of claim 11, wherein said ground coir comprises coir dust and short coir fibers.
13. The method of claim 12, further comprising grinding said coir to pass through a mesh screen ranging in size from between ⅛ of an inch to 1 inch.
14. The method of claim 11, further comprising forming said maintained compressed shape into an irregular shape.
15. The method of claim 12, wherein said irregular shape comprises a non-symmetrical shape.
16. The method of claim 12, further comprising forming said growing medium into a wafer, pellet, brick, slab, cube or triangle.

17. The method of claim 12, further comprising adding a fertilizer, a pesticide, an insecticide, or a fungicide to said growing medium.

18. The method of claim 12, further comprising adding seeds to said compressed growing medium.

19. The method of claim 12, further comprising agitating said bulking agent and said non-ionic surfactant or emulsifier prior to said compression.

20. A method of making a growing medium including dehydrated coir having less than 18% moisture content and a grind size between ⅛ inch mesh and 1 inch mesh, comprising:

blending said dehydrated coir with a non-ionic surfactant or emulsifier;

compressing said dehydrated coir and said non-ionic surfactant or emulsifier to a volume-to-volume ratio greater than about 5:1; and forming said compressed growing medium into an irregular shape;

wherein said compressed dehydrated coir and said non-ionic surfactant or emulsifier forms a matrix, is free of a water soluble binder material, and maintains said irregular compressed shape until hydrated.

\* \* \* \* \*